United States Patent
Miyajima et al.

(10) Patent No.: US 6,437,196 B1
(45) Date of Patent: Aug. 20, 2002

(54) PROCESS FOR PRODUCING GLYCERYL ETHER

(75) Inventors: Tetsuya Miyajima; Mitsuru Uno, both of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/646,749

(22) PCT Filed: Jan. 25, 2000

(86) PCT No.: PCT/JP00/00345

§ 371 (c)(1),
(2), (4) Date: Sep. 22, 2000

(87) PCT Pub. No.: WO00/43340

PCT Pub. Date: Jul. 27, 2000

(30) Foreign Application Priority Data

Jan. 25, 1999 (JP) .......................................... 11-015349

(51) Int. Cl.[7] .............................................. C07C 41/03
(52) U.S. Cl. ...................................................... 568/680
(58) Field of Search ........................................ 568/680

(56) References Cited

U.S. PATENT DOCUMENTS 3,933,923 A * 1/1976 Osberghaus et al. .... 260/615 R
4,465,869 A * 8/1984 Takaishi et al. ............. 568/672
4,634,719 A * 1/1987 Takaishi et al. ............. 514/772
6,207,845 B1 * 3/2001 Okutsu et al. ............... 556/177

FOREIGN PATENT DOCUMENTS

JP       06025052 A2 *  2/1994
JP       06025053 A2 *  2/1994

* cited by examiner

Primary Examiner—Rosalynd Keys
(74) Attorney, Agent, or Firm—Oblon, Spivak, McCleland, Maier & Neustadt, P.C.

(57) ABSTRACT

A process for producing a glyceryl ether which contains a markedly small amount of organohalogen compounds and therefore can be used even for cosmetics and body detergents. The process comprises reacting an alcohol with an α-epihalohydrin in the presence of an acid catalyst, subjecting the reaction mixture to ring closure to convert it into the corresponding glycidyl ether and then hydrolyzing the glycidyl ether, wherein: (a) the hydrolysis is effected at 140 to 230° C. in the presence of a salt formed from a strongly basic compound and a weakly acidic compound, or (b) the reaction mixture after the hydrolysis is heated at 100 to 230° C. in the presence of a salt formed from a strongly basic compound and a weakly acidic compound.

19 Claims, No Drawings

PROCESS FOR PRODUCING GLYCERYL ETHER

This application is a 371 of PCT/JP00/00345 filed Jan. 25, 2000.

TECHNICAL FIELD

The present invention relates to a process for producing a glyceryl ether having a low organohalogen compound content.

BACKGROUND ART

Glyceryl ethers are generally produced by a process comprising three steps, that is, a first step for reacting an alcohol with an α-epihalohydrin in the presence of an acid catalyst such as sulfuric acid, tin tetrachloride or boron trifluoride-ether complex, thereby obtaining a halohydrin ether; a second step for subjecting the halohydrin ether to intramolecular ring closure by using an alkali, thereby obtaining the corresponding glycidyl ether, and a third step for subjecting the glycidyl ether to hydrolysis or the like treatment. In the first step for addition reaction of the epihalohydrin, however, a 2-mole adduct of the epihalohydrin and an isomer of the halohydrin ether different in alcohol added position are inevitably produced. Since these 2-mole adduct, isomer and the like which are organohalogen compounds cannot be decomposed by the intramolecular ring closure of the second step and even in the third step for converting the glycidyl ether to the corresponding glyceryl ether by a known method (Japanese Patent Application Laid-Open No. SHO 49-86307, SHO 56-133281, HEI 5-32578, or the like), they are hard to be hydrolyzed, the glyceryl ether thus obtained necessarily contains organohalogen compounds.

Such glyceryl ether having a high organohalogen compound content is not suited for use in cosmetics, body detergents and the like which are brought into direct contact with a body upon application.

As means for removing or decomposing such organohalogen compounds, purification or decomposition by a strong alkali can be considered. However, the above-described halohydrin ether different in alcohol added position has physical properties, such as boiling point, close to those of the target glyceryl ether, which makes it difficult to remove it by ordinary purification such as distillation. It is possible to decompose it by adding thereto a strong alkali such as NaOH or KOH, followed by heating, but this means is not preferred, because it causes severe coloration and also a partial decomposition of the target glyceryl ether.

In Japanese Patent Application Laid-Open No. HEI 6-25052, disclosed is a process for reducing an organochlorine content by synthesizing a glyceryl ester and then subjecting it to alkali hydrolysis in the presence of an alcohol. This process which requires a fatty acid in an amount not less than an equivalent mole, however, is by no means economical.

DISCLOSURE OF THE INVENTION

It is an object of the present invention to provide an economical process for producing a glyceryl ether.

It is another object of the invention to provide a process for producing a glyceryl ether which has a markedly low organohalogen compound content.

The present inventors have discovered that the organohalogen compound formed upon preparation of a glycidyl ether can be decomposed by heating the glycidyl ether or a glyceryl ether to a predetermined temperature in the presence of a salt formed from a strongly basic compound and a weakly acidic compound.

The present invention therefore provides a process for producing a glyceryl ether comprising reacting an alcohol with an α-epihalohydrin in the presence of an acid catalyst, subjecting the reaction mixture to ring closure, thereby converting it to the corresponding glycidyl ether and then hydrolyzing the resulting glycidyl ether into the corresponding glyceryl ether, wherein (a) the glycidyl ether is hydrolyzed at 140 to 230° C. in the presence of a salt formed from a strongly basic compound and a weakly acidic compound or (b) the reaction mixture after hydrolysis is heated at 100 to 230° C. in the presence of a salt formed from a strongly basic. compound and a weakly acidic compound.

The present invention also provides a process for producing a glyceryl ether, comprising:
  hydrolyzing a glycidyl ether at 140 to 230° C. in the presence of a salt formed from a strongly basic compound and a weakly acidic compound.

The present invention also provides a process for producing a glyceryl ether, comprising:
  hydrolyzing a glycidyl ether, followed by
  heating the reaction mixture at 100 to 230° C. in the presence of a salt formed from a strongly basic compound and a weakly acidic compound.

The present invention also provides a method of reducing the content of organohalogen compound(s) of a glyceryl ether, comprising:
  hydrolyzing a glycidyl ether at 140 to 230° C. in the presence of a salt formed from a strongly basic compound and a weakly acidic compound.

The present invention also provides a method of reducing the content of organohalogen compound(s) of a glyceryl ether, comprising:
  heating a glyceryl ether containing organohalogen compound(s) at 100 to 230° C. in the presence of water and a salt formed from a strongly basic compound and a weakly acidic compound.

BEST MODES FOR CARRYING OUT OF THE INVENTION

A more complete appreciation of the invention and many of the attendant advantages thereof will be readily obtained as the same becomes better understood by reference to the following detailed description.

First, in the present invention, an alcohol and an α-epihalohydrin are reacted in the presence of an acid catalyst, thereby producing a halohydrin ether.

Examples of the alcohol which may be used in the present invention include those represented by the following formula (1):

$$R-(OA)_p-OH \quad (1)$$

where
  R represents a saturated or unsaturated, linear or branched $C_{1-36}$ hydrocarbon group,
  A represents a $C_{2-4}$ alkylene group, and
  p is 0 to 100.

The alcohols where R has 4 to 22 carbon atoms, particularly 4 to 18 carbon atoms, are preferred. Specific examples include saturated aliphatic alcohols such as butanol, pentanol, hexanol, heptanol, octanol, nonanol, decanol, undecanol, dodecanol, tridecanol, tetradecanol, pentadecanol, hexadecanol, heptadecanol, octadecanol, 2-ethylhexanol and 3,5,5-trimethylhexanol, and unsaturated aliphatic alcohols such as oleyl alcohol and linoleyl alcohol, and alkylene oxide adducts thereof. In the formula (1), A preferably represents ethylene, while p preferably stands for 0 to 20, with 0 being particularly preferred.

Examples of the α-epihalohydrin usable in the present invention include α-epichlorohydrin, α-epibromohydrin and α-epiiodohydrin, of which the α-epichlorohydrin is particularly preferred from the viewpoint of easy availability.

As the acid catalyst, usable in the present invention are, as well as Brønsted acids such as hydrochloric acid and sulfuric acid, metal compounds containing at least one element such as boron, aluminum, silicon, titanium, iron, cobalt, zinc, zirconium, tin, antimony or the like which are so-called Lewis acids. Specific examples of the Lewis acid include boron trifluoride-ether complex, boron trifluoride-acetic acid complex, boron trifluoride-phenol complex , aluminum chloride, aluminum bromide, zinc chloride, tin tetrachloride, antimony chloride, titanium tetrachloride, silicon tetrachloride, ferric chloride, ferric bromide, cobalt (II) chloride, cobalt (II) bromide, zirconium chloride, boron oxide and acidic active alumina.

When such a Lewis acid is employed, the reaction can be effected without or after removal of water from the system in a conventional manner, but the latter one is preferred because it brings about an increase in both the reaction rate and yield.

The catalyst is used in an amount of 0.001 to 0.1 mole per mole of the alcohol, with 0.005 to 0.05 mole being particularly preferred.

The formation of a halohydrin ether from an alcohol and an α-epihalohydrin may be conducted in an ordinary manner, described specifically, by reacting, with the alcohol, the α-epihalohydrin which is used in an amount of 0.5 to 1.5 moles, preferably 0.6 to 1.2 moles per mole of the alcohol, in the presence of the above-exemplified acid catalyst at a temperature of 10 to 150° C., preferably 70 to 120° C. for 0.5 to 10 hours.

From the halohydrin ether obtained by the above-described reaction, the corresponding glycidyl ether and then glyceryl ether may be prepared by removing the catalyst and unreacted raw materials from the reaction mixture if necessary, adding an alkali to the residue, subjecting the resulting mixture to ring closure by dehydrohalogenation and hydrolyzing the dehydrohalogenated product.

Here, ring closure and hydrolysis can be carried out either separately or simultaneously.

When ring closure and hydrolysis are carried out separately, the remaining raw material alcohol and epihalohydrin may be removed by known separating and purifying means such as distillation, washing, recrystallization or column chromatography after completion of the ring closure reaction; or hydrolysis may be effected without removal.

Exemplary alkalis usable in ring closure reaction include hydroxides of an element of Group 1A such as sodium hydroxide and potassium hydroxide and hydroxides of an element of Group 2A such as calcium hydroxide and barium hydroxide. Among them, sodium hydroxide and potassium hydroxide are particularly preferred. The alkali is preferably used in an amount of 1.0 to 4.0 moles, particularly 1.0 to 2.5 moles per mole of the epihalohydrin. The alkali is preferably added, for example, in the form of a 10 to 50% aqueous solution. The reaction is preferably conducted at 40 to 200° C. for 0.1 to 20 hours.

The glyceryl ether is available by hydrolyzing the glycidyl ether, which has been obtained in the above-described reaction, by a known manner using an aqueous solution of an acid or alkali.

Examples of the acid or alkali employed for hydrolysis include mineral acids such as hydrochloric acid and sulfuric acid, hydroxides of a Group 1A element of the periodic table such as sodium hydroxide and potassium hydroxide, hydroxides of a Group 2A element such as calcium hydroxide and barium hydroxide, carbonates of a Group 1A element such as sodium carbonate, sodium bicarbonate and potassium carbonate and carbonates of a Group 2A element such as calcium carbonate and magnesium carbonate. Among them, the carbonates of a Group 1A element such as sodium carbonate, sodium bicarbonate and potassium carbonate are preferred from the viewpoint of the selectivity of the reaction.

Water is used in an amount of 1 to 100 mole equivalents per mole of the glycidyl ether, of which the amount of 2 to 10 mole equivalents is particularly preferred from the viewpoint of the selectivity of the reaction and productivity.

The above-described hydrolysis using an acid or alkali can be carried out within a temperature range of 50 to 250° C. under normal pressure or under pressure. From the viewpoints of a reaction rate and stability of the compound, the hydrolysis is preferably conducted at 80 to 200° C. for 0.1 to 30 hours.

Alternatively, the glycidyl ether can be hydrolyzed, for example, in accordance with the process (Japanese Patent Application Laid-Open No. Hei 5-32578, incorporated herein by reference) using phosphoric acid or activated clay as an acid catalyst and an N,N-substituted amide as a solvent, or the process (Japanese Patent Application Laid-Open No. Hei 7-53431, incorporated herein by reference) wherein the hydrolysis is effected in the presence of a tertiary amine. In the latter process, the hydrolysis is conducted at a temperature not greater than 140° C. from the viewpoint of stability. It is also possible to hydrolyze the glycidyl ether through a fatty acid ester, dioxolan or the like.

The present invention is characterized by decomposing the organohalogen compound, which exists with the glycidyl ether, upon or after hydrolysis thereof.

In the case of decomposing the organohalogen compound after hydrolysis, the reaction mixture is heated at 100 to 230° C., preferably 130 to 200° C., more preferably 150 to 200° C. in the presence of a salt formed from a strongly basic compound and a weakly acidic compound, followed by stirring for 0.1 to 100 hours.

Decomposition of the organohalogen compound upon hydrolysis, on the other hand, can be attained by heating the reaction mixture at 140 to 230° C., preferably 140 to 200° C., more preferably 180 to 200° C. in the presence of a salt formed from a strongly basic compound and a weakly acidic compound for 0.1 to 100 hours.

Even in the process (Japanese Patent Application Laid-Open No. Hei 7-53431) wherein the hydrolysis of the glycidyl ether is effected in the presence of a tertiary amine, the organohalogen compound can be decomposed by the reaction at a temperature not less than 140° C. The resulting quaternary ammonium salt formed in the system, however, is unstable at a high temperature not less than 140° C. and it is decomposed in the system to form a low-molecular-weight amine, which becomes a cause for odor and coloration.

Illustrative of the salt used in the decomposition of the organohalogen compound include salts formed from a weakly acidic compound such as carboxylic acid, phosphoric acid or carbonic acid with a Group 1A element of the periodic table such as sodium or potassium or a Group 2A element such as magnesium or calcium. Among them, salts of a $C_{1-22}$, particularly $C_{1-18}$ carboxylic acid and those of carbonic acid are preferred. Specific examples of the weakly acidic compound include saturated or unsaturated $C_{1-22}$ fatty acids such as acetic acid, propionic acid, butyric acid, octanoic acid,. lauric acid and oleic acid, $C_{2-18}$ dicarboxylic acids such as succinic acid, adipic acid, glutaric acid and dodecandioic acid, oxycarboxylic acids such as lactic acid, malic acid and citric acid, carbonic acid and acid carbonate. Among them, $C_{2-12}$ fatty acids and dicarboxylic acids such as acetic acid, octanoic acid, lauric acid and adipic acid are preferred from the viewpoints of reactivity, cost and yield. Particularly preferred are acetic acid and lauric acid.

Accordingly, the compound may be formed from an ion of a metal element from Group 1A or 2A and a weakly acidic compound.

The salt formed from such a strongly basic compound and a weakly acidic compound may be added in the form of a salt or alternatively, the salt may be formed in the reaction system by adding them thereto.

The salt is preferably used in an amount of 0.1 to 50 moles, more preferably 0.5 to 10 moles, particularly 1 to 5 moles per mole of the organohalogen compound contained in the glycidyl ether. Here, the amount of the compound of the organohalogen compound contained in the glycidyl ether is determined by gas chromatography.

The glyceryl ether thus obtained can be isolated and purified by known isolating and purifying procedures, such as, for example, distillation, washing, recrystallization, column chromatography, or the like.

EXAMPLES

Having generally described this invention, a further understanding can be obtained by reference to certain specific examples which are provided herein for purposes of illustration only and are not intended to be limiting unless otherwise specified.

Example 1

Dodecanol (167.4 g) and 8.1 g of trifluoromethanesulfonic acid were heated to 95° C. while stirring. To the reaction mixture, 166.5 g of epichlorohydrin was added dropwise over 1 hour, followed by stirring for 8 hours. After completion of the reaction, the reaction mixture was cooled to 50° C. Over 1 hour, 75 g of a 48% aqueous solution of sodium hydroxide was added dropwise at a temperature maintained at 50° C. After stirring for 3 hours, 120 mL of water was added to the reaction mixture to cause separation. The water layer thus occurred was removed. The residue was then washed twice with 100 mL of water, whereby 249 g of crude dodecyl glycidyl ether was obtained.

In an autoclave, 249 of the resulting dodecyl glycidyl ether, 97.2 g of water and 34.8 g of sodium bicarbonate were charged and were stirred at 200° C. for 8 hours. After completion of the reaction, the reaction mixture was dehydrated at 120° C. under reduced pressure (6.67 kPa), followed by purification by distillation under reduced pressure (13 to 26 Pa, 160 to 170° C.), whereby 117 g of monododecyl glyceryl ether was obtained. As a result of gas chromatographic analysis (hereinafter abbreviated as "GLC"), it was found that the resulting product had a purity not less than 99% and the content of a chlorohydrin ether isomer different in alcohol added position and a 2-mole adduct of epichlorohydrin (hereinafter called "organochlorine compounds", for simplicity) was not greater than 100 ppm.

Example 2

Octanol (130 g) and 2.84 g of a boron trifluorideether complex were cooled to 0° C. while stirring. At a temperature maintained at 0° C., 138.8 g of epichlorohydrin was added dropwise over 1 hour. After completion of dropwise addition, an excess alcohol was distilled off at 100° C. under reduced pressure (13 to 26 Pa). The reaction mixture was cooled to 50° C. and while maintaining the temperature at 50° C., 125 g of a 48% aqueous solution of sodium hydroxide was added dropwise over 1 hour. After stirring for 3 hours, 200 mL of water was added to the reaction mixture to cause separation. The water layer thus obtained was removed and then the residue was washed twice with 100 mL of water, whereby 208 g of crude octyl glycidyl ether was obtained.

In an autoclave, 208 g of the resulting crude octyl glycidyl ether, 104.8 g of water, 5.82 g of lauric acid and 18.5 g of potassium hydroxide were charged. The resulting mixture was stirred at 140° C. for 5 hours. The reaction mixture was dehydrated at 100° C. under reduced pressure (6.67 kPa), followed by the addition of 9.7 g of lauric acid and 2.72 g of potassium hydroxide. After reaction at 160° C. for 15 hours, the reaction mixture was purified by distillation under reduced pressure (53 to 67 Pa, 120 to 123° C.), whereby 110.2 g of monooctyl glyceryl ether was obtained. As a result of GLC, it was found that the resulting product had a purity not less than 99% and the content of organochlorine compounds was not greater than 100 ppm.

Example 3 n-Pentanol (88 g) and 6.82 g of zinc chloride were heated to 100° C. while stirring, followed by the dropwise addition of 138.8 g of epichlorohydrin over 1 hour. The reaction mixture was heated to 115° C. and reacted for 5 hours. After completion of the reaction, the reaction mixture was cooled to 50° C. While maintaining the temperature at 50° C., 92 g of a 48% aqueous solution of sodium hydroxide was added dropwise over 1 hour. After stirring for 3 hours, 150 mL of water was added to the reaction mixture to cause separation. The water layer thus formed was then removed and the residue was washed twice with 100 mL of water, whereby 163 g of crude pentyl glycidyl ether was obtained.

In an autoclave, 163 g of the crude pentyl glycidyl ether, 108 g of water, 7.3 g of adipic acid and 10.4 g of sodium hydroxide were charged. The resulting mixture was heated to 200° C. while stirring. After stirring for 2 hours, 1.6 g of sodium hydroxide was added. The resulting reaction mixture was dehydrated at 100° C. under reduced pressure (5.32 kPa), followed by purification by distillation under reduced pressure (133 to 266 Pa, 114 to 115° C.), whereby 117 g of monopentyl glyceryl ether was obtained. As a result of GLC, it was found that the resulting compound had a purity not less than 99% and the content of organochlorine compounds was not greater than 100 ppm.

Example 4 n-Pentanol (132 g) and 8.1 g of ferric chloride were heated to 100° C. while stirring, followed by the dropwise addition of 92.5 g of epichlorohydrin over 1 hour. The reaction mixture was then heated to 115° C. and reacted for 5 hours. After the removal of an excess alcohol at 100° C. under reduced pressure (5.32 kPa), 6 g of lauric acid, 118 g of a 48% aqueous solution of potassium hydroxide and 162 g of water were added to the residue. The resulting mixture was reacted at 200° C. for 5 hours in an autoclave. The reaction mixture was neutralized with 2.3 g of a 48% aqueous solution of potassium hydroxide. The reaction mixture was dehydrated at 100° C. under reduced pressure (6.67 kPa) and the residue was purified by distillation under reduced pressure (133 to 266 Pa, 114 to 115° C.), whereby 102 g of monopentyl glyceryl ether was obtained. As a result of GLC, it was found to that the resulting compound had a purity not less than 99% and the content of organochlorine compounds was not greater than 100 ppm.

Example 5

To a mixture of 406 g of acetone and 10 g of boron trifluoride, 163 g of n-pentyl glycidyl ether obtained in a similar manner to Example 3 was added dropwise over 2 hours while cooling to maintain the temperature at 20 to 30° C. After reaction for 1 hour, the reaction mixture was poured into a large amount of a diluted aqueous solution of sodium bicarbonate for neutralization. Diethyl ether was added and the resulting mixture was stirred. The reaction mixture was allowed to stand to cause separation. The diethyl ether layer thus separated was dehydrated by the addition of sodium sulfate. From the residue, the solid was removed by filtration and then, the solvent was distilled off from the filtrate at room temperature under reduced pressure (133 Pa). To 215 g of 2,2-dimethyl-4-pentyloxymethyl-1,3-dioxolane thus obtained, 1000 mL of ethanol and 1000 mL of 0.1 N sulfuric acid were added. While stirring, the resulting mixture was heated to 80° C. After reaction for 10 hours, the reaction mixture was cooled to room temperature. The solution thus obtained was treated twice with 1000 mL of diethyl ether to extract an oil layer. To the extracted oil layer was added an aqueous solution of sodium bicarbonate, and the remaining acid was thereby neutralized. After separation and removal of the resulting water layer, and diethyl ether was distilled off, 20 g of sodium acetate was added to the residue. The resulting mixture was heated to 180° C. and stirred for 5 hours. After neutralization with 16.8 g of sodium bicarbonate, purification was effected by distillation under reduced pressure (133 to 266 Pa, 114 to 115° C.), whereby 108.7 g of monopentyl glyceryl ether was obtained. As a result of GLC, it was found that the resulting compound had a purity not less than 99% and the content of organochlorine compounds was not greater than 100 ppm.

Example 6

In a reactor, 390 g of octanol, 2 g of aluminum triisopropoxide and 1.4 g of sulfuric acid were charged. After heating to 100° C., dehydration was conducted under reduced pressure (2.67 kPa). The residue was then cooled to 85° C., followed by the dropwise addition of 185 g of epichlorohydrin at a temperature maintained at 85° C. After stirring at 85° C. for 4 hours, an excess alcohol was removed at 100° C. under reduced pressure (0.67 kPa). To the crude octyl halohydrin ether thus obtained, 480 g of a 209 aqueous solution of sodium hydroxide was added and the resulting mixture was reacted at 90° C. for 2 hours. After completion of the reaction, the water layer was removed, whereby 315 g of crude octyl glycidyl ether was obtained. In an autoclave, 200 g of the resulting crude octyl glycidyl ether, 35 g of water, 11.8 g of 99% acetic acid and 12.1 g of a 48% aqueous solution of sodium hydroxide were charged, followed by stirring at 200° C. for 1 hour. At a temperature maintained at 200° C., 27.5 g of a 48% aqueous solution of sodium hydroxide was added dropwise over 3 hours and reaction was conducted for 1 hour. The reaction mixture was cooled to 80° C. While maintaining the temperature at 80° C., 150 g of water was added and the resulting mixture was stirred vigorously. The reaction mixture was allowed to stand to cause separation, followed by removal of the water layer. The operation from the addition of 150 g of water to the separation was then repeated three times. The reaction mixture was dehydrated at 100° C. under reduced pressure (5.32 kPa), whereby 224 g of monooctyl glyceryl ether was obtained. As a result of GLC, it was found that the resulting product had a purity of 91% and the content of organochlorine compounds was not greater than 100 ppm.

Comparative Example 1

In an autoclave, 200 g of crude octyl glycidyl ether obtained in a similar manner to Example 2, 100 g of dimethyl formamide and 65 g of water were charged. After the addition of 5 g of activated clay, the resulting mixture was reacted at 135° C. for 8 hours. After completion of the reaction, the catalyst was removed by filtration and water and the solvent were distilled off at 100° C. under reduced pressure (2.7 kPa). The residue was then purified under reduced pressure (53 to 67 Pa, 120 to 123° C.), whereby 95 g of monooctyl glyceryl ether was obtained. As a result of GLC, it was found that the resulting compound had a purity of 97% and the content of organochlorine compounds was 3%.

Comparative Example 2

In an autoclave, 145 g of crude pentyl glycidyl ether obtained in a similar manner to Example 3, 300 g of THF, 10 g of triethylamine and 36 g of water were charged. The resulting mixture was reacted at 140° C. for 20 hours. After completion of the reaction, the reaction mixture was neutralized with sulfuric acid and water and the solvent were distilled off at 100° C. under reduced pressure (5.3 kPa). The residue was then purified by distillation under reduced pressure (133 to 266 Pa, 114 to 115° C.), whereby 138 g of monopentyl glyceryl ether was obtained. As a result of GLC, it was found that the resulting compound had a purity not less than 98% and the content of organochlorine compounds was not greater than 100 ppm. The resulting compound was however not suited for use because slight coloring and amine odor were observed.

Capability of Exploitation in Industry

According to the present invention, a glyceryl ether which contains a markedly small amount of organohalogen compounds can be produced. Such a glyceryl ether can be used for various applications such as solvents, cosmetics, detergents, emulsifiers, humectants, moisturizers and oil agents. Particularly, it can be used suitably for cosmetics, body detergents and the like.

Obviously, numerous modifications and variations of the present invention are possible in light of the above teachings. It is therefore to be understood that within the scope of the appended claims, the invention may be practiced otherwise than as specifically described herein.

What is claimed is:

1. In a process for producing a glyceryl ether, which comprises reacting an alcohol with an α-epihalohydrin in the presence of an acid catalyst, subjecting the reaction mixture to ring closure to convert the mixture into the corresponding glycidyl ether and then hydrolyzing the resulting glycidyl ether, the improvement comprising:

heating the reaction mixture after hydrolysis in the presence of a salt formed from a strongly basic compound and a weakly acidic compound at 100 to 230° C.

2. The process of claim 1, wherein the salt formed from a strongly basic compound and a weakly acidic compound is a salt of a Group 1A or Group 2A element with a carboxylic acid, phosphoric acid or carbonic acid.

3. The process of claim 1, wherein the salt formed from a strongly basic compound and a weakly acidic compound is a salt of a Group 1A or Group 2A element with a $C_{2-12}$ fatty acid.

4. The process of claim 1, wherein the strongly basic compound is a Group 1A or Group 2A element.

5. The process of claim 4, wherein the element is sodium, potassium, magnesium or calcium.

6. The process of claim 1, wherein the weakly acidic compound is a carboxylic acid, phosphoric acid or carbonic acid.

7. The process of claim 1, wherein the amount of organohalogen compound contained in the glycidyl ether is determined.

8. The process of claim 7, wherein the salt formed from a strongly basic compound and a weakly acidic compound is used in an amount of 0.5 to 10 moles per mole of the organohalogen compound contained in the glycidyl ether.

9. The process of claim 7, wherein the salt formed from a strongly basic compound and a weakly acidic compound is used in an amount of 1 to 5 moles per mole of the organohalogen compound contained in the glycidyl ether.

10. A process for producing a glyceryl ether, comprising:
   hydrolyzing a glycidyl ether, followed by
   heating the reaction mixture at 100 to 230° C. in the presence of a salt formed from a strongly basic compound and a weakly acidic compound.

11. The process of claim 10, wherein the glycidyl ether is produced by a process comprising:
   reacting an alcohol with an α-epihalohydrin in the presence of an acid catalyst, followed by
   subjecting the reaction mixture to ring closure to convert the mixture into the corresponding glycidyl ether.

12. The process of claim 10, wherein the salt formed from a strongly basic compound and a weakly acidic compound is a salt of a Group 1A or Group 2A element with a carboxylic acid, phosphoric acid or carbonic acid.

13. The process of claim 10, wherein the salt formed from a strongly basic compound and a weakly acidic compound is a salt of a Group 1A or Group 2A element with a $C_{2-12}$ fatty acid.

14. The process of claim 10, wherein the strongly basic compound is a Group 1A or Group 2A element.

15. The process of claim 14, wherein the element is sodium, potassium, magnesium or calcium.

16. The process of claim 10, wherein the weakly acidic compound is a carboxylic acid, phosphoric acid or carbonic acid.

17. The process of claim 10, wherein the amount of organohalogen compound contained in the glycidyl ether is determined.

18. The process of claim 17, wherein the salt formed from a strongly basic compound and a weakly acidic compound is used in an amount of 0.5 to 10 moles per mole of the organohalogen compound contained in the glycidyl ether.

19. The process of claim 17, wherein the salt formed from a strongly basic compound and a weakly acidic compound is used in an amount of 1 to 5 moles per mole of the organohalogen compound contained in the glycidyl ether.

* * * * *